(12) United States Patent
Takahashi et al.

(10) Patent No.: US 9,353,288 B2
(45) Date of Patent: May 31, 2016

(54) ORGANOSILICON COMPOUND, THIN FILM FORMING COMPOSITION USING SAME, AND ORGANIC THIN FILM

(71) Applicant: NIPPON SODA CO., LTD., Tokyo (JP)

(72) Inventors: Toshiaki Takahashi, Chiba (JP); Tomoya Hidaka, Chiba (JP); Daisuke Asanuma, Niigata (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/405,270

(22) PCT Filed: Jul. 2, 2013

(86) PCT No.: PCT/JP2013/004104
§ 371 (c)(1),
(2) Date: Dec. 3, 2014

(87) PCT Pub. No.: WO2014/006885
PCT Pub. Date: Jan. 9, 2014

(65) Prior Publication Data
US 2015/0148483 A1 May 28, 2015

(30) Foreign Application Priority Data

Jul. 5, 2012 (JP) .................................. 2012-151802
Aug. 22, 2012 (JP) .................................. 2012-182905

(51) Int. Cl.
| | | |
|---|---|---|
| C08G 77/04 | (2006.01) |
| C09D 183/06 | (2006.01) |
| C07F 7/18 | (2006.01) |
| C08G 77/06 | (2006.01) |
| C08K 3/22 | (2006.01) |
| B05D 1/18 | (2006.01) |
| B05D 5/08 | (2006.01) |

(52) U.S. Cl.
CPC ............... *C09D 183/06* (2013.01); *C07F 7/18* (2013.01); *C07F 7/1804* (2013.01); *C07F 7/1852* (2013.01); *C08G 77/06* (2013.01); *B05D 1/18* (2013.01); *B05D 5/08* (2013.01); *C08K 3/22* (2013.01)

(58) Field of Classification Search
CPC ............................ C07F 7/1852; C09D 183/06
See application file for complete search history.

(56) References Cited

U.S. PATENT DOCUMENTS

| 5,552,236 A | 9/1996 | Ohtake et al. |
| 8,426,019 B2 | 4/2013 | Kimura et al. |
| 2005/0158208 A1 | 7/2005 | Mino et al. |
| 2008/0233292 A1* | 9/2008 | Kusaki et al. ................. 427/331 |

FOREIGN PATENT DOCUMENTS

| JP | H04-132637 A | 5/1992 |
| JP | H06-45142 A | 2/1994 |
| JP | H11-228942 A | 8/1999 |
| JP | 2004-231590 A | 8/2004 |
| JP | 2005-206454 A | 8/2005 |
| JP | 2008-268180 A | 11/2008 |
| WO | 03/023831 A1 | 3/2003 |
| WO | 2004091810 A1 | 10/2004 |

OTHER PUBLICATIONS

Zhao et al., "Synthesis of Polystyrene Brushes on Silicate Substrates via Carbocationic Polymerizaion from Self-Assembled Monolayers," Macromolecules, 2000, vol. 33, pp. 342-348.
Effertz et al., "Design of Novel Dielectric Surface Modifications for Perylene Thin-Film Transistors," Advanced Functional Materials, 2012, vol. 22, pp. 415-420.
Oct. 1, 2013 International Search Report issued in International Patent Application No. PCT/JP2013/004104.
Jan. 6, 2015 International Preliminary Report on Patentability issued in International Application No. PCT/JP2013/004104.
Nov. 3, 2015 Extended European Search Report issued in European Application No. 13812652.9.

* cited by examiner

*Primary Examiner* — Margaret Moore
(74) *Attorney, Agent, or Firm* — Oliff PLC

(57) ABSTRACT

The present invention is intended to provide an organosilicon compound for forming a novel organic thin film having improved physical properties. An organosilicon compound of the present invention is an organosilicon compound represented by formula (I) R—$(CH_2)_n$—$SiX_3$ (I) (wherein R represents an alkoxy group having 1 to 3 carbon atoms or a phenyl group that optionally has a substituent, X represents a hydroxyl group or a hydrolyzable group, and n represents any integer from 17 to 24). An organic thin film can be formed by mixing the aforementioned organosilicon compound, a compound that can interact with the organosilicon compound, and water in an organic solvent to prepare an organic thin film forming solution, and bringing the organic thin film forming solution into contact with a substrate.

4 Claims, No Drawings

ORGANOSILICON COMPOUND, THIN FILM FORMING COMPOSITION USING SAME, AND ORGANIC THIN FILM

TECHNICAL FIELD

The present invention relates to a novel organosilicon compound, a thin film forming composition using the same, and an organic thin film. The present application claims priority to Japanese Patent Application No. 2012-151802 filed on Jul. 5, 2012 and Japanese Patent Application No. 2012-182905 filed on Aug. 22, 2012, the contents of which are incorporated herein.

BACKGROUND ART

Surfaces of substrates consisting of glass, metal, plastics, ceramics, and the like have conventionally been modified in various fields, depending on purposes. For example, in order to impart water repellency and oil repellency on surfaces of glass and plastics, it is known that a liquid containing an organic metal compound such as a fluorine-containing silane coupling agent or a hydrolyzate of an organic metal compound is brought into contact with a base material surface to form an organic thin film.

Examples of the organic metal compound for forming an organic thin film known include the following organic metal compounds:

(1) $F(CF_2)_m(CH_2)_nSiR_qX_{3-q}$ (wherein m=1 to 15, n=0 to 15, m+n=10 to 30, and R represents an alkyl group) and $F(CF_2)_m(CH_2)_nA(CH_2)_pSi(CH_3)_qX_{3-q}$ (wherein m=1 to 8, n=0 to 2, p=5 to 25, q=0 to 2, and A represents an oxygen atom (—O—), carboxy (—COO—), or dimethylsilylene (—Si(CH$_2$)$_2$—)) (patent document 1).

(2) A metal surfactant represented by

$R^1_nMX_{m-n}$ (wherein $R^1$ represents a hydrocarbon group that optionally has a substituent, a halogenated hydrocarbon group that optionally has a substituent, a hydrocarbon group comprising a linking group, or a halogenated hydrocarbon group comprising a linking group, M represents at least one metal atom selected from the group consisting of a silicon atom, a germanium atom, a tin atom, a titanium atom, and a zirconium atom, X represents a hydroxyl group or a hydrolyzable group, n represents any integer from 1 to (m−1), m represents the atomic valence of M, $R^1$ may be identical or different in the case where n is 2 or more, and X may be identical or different in the case where (m−n) is 2 or more; provided that at least one X of (m−n) X's is a hydrolyzable group) (patent document 2).

(3) A silane derivative represented by the formula

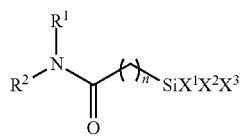

(wherein n represents an integer from 1 to 20, $R^1$ represents an alkyl group having 1 to 20 carbon atoms, an fluoroalkyl group having 1 to 20 carbon atoms, a phenyl group optionally having a substituent, or a benzyl group optionally having a substituent, $R^2$ represents an aromatic group having a nitro group on the ortho position, and $X^1$ to $X^3$ each independently represent a halogen atom or an alkoxy group having 1 to 5 alkoxy group) (patent document 3).

(4) A fluoroalkylalkoxysilane compound or a fluoroalkyl halogenated silane compound, such as $CF_3CH_2CH_2Si(OR)_3$, $CF_3(CF_2)_5CH_2CH_2Si(OR)_3$, $CF_3(CF_2)_5CH_2CH_2SiR(OR)_2$, $CF_3(CF_2)_7CH_2CH_2Si(OR)_3$, $CF_3(CF_2)_7CH_2CH_2SiR(OR)_2$, $CF_3CH_2CH_2SiCl_3$, $CF_3(CF_2)_5CH_2CH_2SiCl_3$, $CF_3(CF_2)_5CH_2CH_2SiRCl_2$, $CF_3(CF_2)_7CH_2CH_2SiCl_3$, $CF_3(CF_2)_7CH_2CH_2SiRCl_2$ (patent document 4).

PRIOR ART DOCUMENTS

Patent Documents

Patent Document 1: Japanese unexamined Patent Application Publication No. 04-132637
Patent Document 2: Japanese unexamined Patent Application Republication (Translation of PCT Application) No. 2004-91810
Patent Document 3: Japanese unexamined Patent Application Publication No. 2004-231590
Patent Document 4: Japanese unexamined Patent Application Publication No. 11-228942

SUMMARY OF THE INVENTION

Object to be Solved by the Invention

The organic metal compounds described in the above documents and the like are useful as organic thin films, but organic thin films having further improved physical properties have been required.

Thus, it is an object of the present invention is to provide an organosilicon compound for forming a novel organic thin film having improved physical properties.

Means to Solve the Object

The present inventors, as a result of intensive studies to solve the above problem, have found that introduction of a specific substituent on the end of an organosilicon compound known so far provides an organic thin film having improved physical properties, thereby having completed the present invention.

That is, the present invention relates to
(1) an organosilicon compound represented by formula (I):

R—(CH$_2$)$_n$—SiX$_3$ (I)

(wherein R represents an alkoxy group having 1 to 3 carbon atoms or a phenyl group that optionally has a substituent, X represents a hydroxyl group or a hydrolyzable group, and n represents any integer from 17 to 24), (2) an organic thin film forming solution obtained by mixing the organosilicon compound represented by formula (I) according to above (1), a compound that can interact with the organosilicon compound, and water in an organic solvent, (3) a method for forming an organic thin film comprising the steps of:

(A) mixing
a) the organosilicon compound represented by formula (I) according to (1),
b) a compound that can interact with the organosilicon compound, and
c) water in an organic solvent to prepare an organic thin film forming solution; and (B) bringing the obtained organic thin film forming solution into contact with a substrate, (4) an organic thin film obtained by the method according to (3), and (5) the organic thin film according to (4), wherein the organic thin film is a crystalline monolayer.

Effect of the Invention

A compound for forming an organic thin film has been enabled to be provided, wherein the organic thin film has useful characteristics different from conventional ones, from the viewpoints of liquid repellency, liquid slippage, peelability, lubricity, and the like.

MODE OF CARRYING OUT THE INVENTION (1) Organosilicon Compound (Organosilicon Compound)

An organosilicon compound of the present invention is represented by the following formula (I):

Formula (I)

$$R-(CH_2)_n-SiX_3 \quad (I)$$

wherein R represents an alkoxy group having 1 to 3 carbon atoms or a phenyl group that optionally has a substituent, X represents a hydroxyl group or a hydrolyzable group, and n represents any integer from 17 to 24. n is more preferably 18 to 22.

Examples of the alkoxy group having 1 to 3 carbon atoms in the above formula (I) include a methoxy group, an ethoxy group, a n-propoxy group, and an isopropoxy group.

The phenyl group optionally has a substituent, and examples of the substituent include an alkyl group (preferably an alkyl group having 1 to 3 carbon atoms) such as methyl and ethyl, an alkoxy group (preferably an alkoxy group having 1 to 3 carbon atoms) such as methoxy and ethoxy, a halogen atom such as a fluorine atom and a chlorine atom, and a cyano group.

X each independently represents a hydroxyl group or a hydrolyzable group. The hydrolyzable group is not particularly limited, provided that it is a group that reacts with water to be decomposed. Examples include an alkoxy group having 1 to 6 carbon atoms that optionally has a substituent; an acyloxy group that optionally has a substituent; a halogen atom such as a fluorine atom, a chlorine atom, a bromine atom, and an iodine atom; an isocyanate group; a cyano group; an amino group; or an amide group.

Examples of the alkoxy group having 1 to 6 carbon atoms include a methoxy group, an ethoxy group, a n-propoxy group, an isopropoxy group, a n-butoxy group, a sec-butoxy group, a t-butoxy group, a n-pentyloxy group, and a n-hexyloxy group. Examples of the acyloxy group include an acyloxy group having 1 to 10 carbon atoms such as a formyloxy group, an acetoxy group, a propionyloxy group, a n-propylcarbonyloxy group, an isopropylcarbonyloxy group, and a n-butylcarbonyloxy group. Examples of these substituents include a carboxyl group, an amide group, an imide group, an ester group, and a hydroxyl group. Of these, X is preferably a hydroxyl group, an alkoxy group having 1 to 4 carbon atoms, an acyloxy group having 1 to 6 carbon atoms, a halogen atom, or an isocyanate group, more preferably an alkoxy group having 1 to 4 carbon atoms or an acyloxy group having 1 to 6 carbon atoms.

Specific examples of the compound represented by formula (I) include those shown below. The following lists, as typical examples, compounds having a silicon atom as the metal atom, but the present invention is not intended to be limited to these compounds.

$CH_3O(CH_2)_{18}Si(OCH_3)_3$,
$CH_3O(CH_2)_{22}Si(OCH_3)_3$,
$C_2H_5O(CH_2)_{18}Si(OCH_3)_3$,
$C_2H_5O(CH_2)_{22}Si(OCH_3)_3$,
$C_6H_5(CH_2)_{18}Si(OCH_3)_3$,
$C_6H_5(CH_2)_{22}Si(OCH_3)_3$,
$CH_3O(CH_2)_{18}Si(OC_2H_5)_3$,
$CH_3O(CH_2)_{22}Si(OC_2H_5)_3$,
$C_2H_5O(CH_2)_{18}Si(OC_2H_5)_3$,
$C_2H_5O(CH_2)_{22}Si(OC_2H_5)_3$,
$C_6H_5(CH_2)_{18}Si(OC_2H_5)_3$,
$C_6H_5(CH_2)_{22}Si(OC_2H_5)_3$,
$CH_3O(CH_2)_{18}SiCl_3$,
$CH_3O(CH_2)_{22}SiCl_3$,
$C_2H_5O(CH_2)_{18}SiCl_3$,
$C_2H_5O(CH_2)_{22}SiCl_3$,
$C_6H_5(CH_2)_{18}SiCl_3$,
$C_6H_5(CH_2)_{22}SiCl_3$,
$CH_3O(CH_2)_{18}Si(NCO)_3$,
$CH_3O(CH_2)_{22}Si(NCO)_3$,
$C_2H_5O(CH_2)_{18}Si(NCO)_3$,
$C_2H_5O(CH_2)_{22}Si(NCO)_3$,
$C_6H_5(CH_2)_{18}Si(NCO)_3$,
$C_6H_5(CH_2)_{22}Si(NCO)_3$,
$CH_3O(CH_2)_{18}Si(OCH_3)_2(OH)$,
$CH_3O(CH_2)_{22}Si(OCH_3)_2(OH)$,
$C_2H_5O(CH_2)_{18}Si(OCH_3)_2(OH)$,
$C_2H_5O(CH_2)_{22}Si(OCH_3)_2(OH)$,
$C_6H_5(CH_2)_{18}Si(OCH_3)_2(OH)$,
$C_6H_5(CH_2)_{22}Si(OCH_3)_2(OH)$
$CH_3O(CH_2)_{18}Si(OH)_3$,
$CH_3O(CH_2)_{22}Si(OH)_3$,
$C_2H_5O(CH_2)_{18}Si(OH)_3$,
$C_2H_5O(CH_2)_{22}Si(OH)_3$,
$C_6H_5(CH_2)_{18}Si(OH)_3$,
$C_6H_5(CH_2)_{22}Si(OH)_3$,
can be listed, but the present invention is not intended to be limited to these compounds.

Alternatively, these compounds can be used singly or in combinations of two or more.

(Method for Producing an Organosilicon Compound)

A compound represented by formula (I) of the present invention can be synthesized by known methods and, for example, can be synthesized as follows.

1) In the Case of a Compound Wherein R is an Alkoxy Group Having 1 to 3 Carbon Atoms The First Step: Reaction of an α-Olefin Compound Having a Halogenated End with an Alcohol Compound (Etherification)

To an alkaline aqueous solution such as sodium hydroxide and a hydrophobic organic solvent (preferably MIBK, toluene, and the like), an α-olefin compound having a halogenated end such as 18-bromo-1-octadecene with an equimolar or excess amount of an alcohol compound is added. The mixture is stirred in the presence of a phase transfer catalyst such as a quaternary ammonium salt at room temperature or with heating as required until the reaction is completed.

After the reaction liquid is washed with distilled water, the organic layer is dried, concentrated to dryness, and then, purified with silica gel column chromatography and the like to obtain an etherified material.

The Second Step: Hydrosilation of the Double Bond of the Etherified Material

The etherified material obtained in the first step and an excess amount of trialkoxysilane are mixed and heated under a nitrogen atmosphere in the presence of a 10% Pt/C catalyst and the like.

After reaction is completed, the catalyst is removed by filtration. Unreacted trialkoxysilane is distilled off under reduced pressure to obtain a trialkoxysilated material.

The Third Step: Alkoxy Exchange

The alkoxysilated material obtained in the second step is subjected to alcohol exchange reaction in alcohol having a small amount of hydrochloric acid dissolved therein to obtain a certain intended organosilicon compound.

2) In the Case of a Compound Wherein R is a Phenyl Group Optionally Having a Substituent The First Step: Reaction of an α-Olefin Compound Having a Halogenated End with Phenylmagnesium Halide To a solution of an α-olefin compound having a halogenated end such as 18-bromo-1-octadecene and the like in dehydrated THF and the like, lithium chloride and copper chloride are added, and stirred and dissolved at room temperature. To this, a phenylmagnesium halide solution is added dropwise at 25 to 35° C. The mixture is stirred until the reaction is completed. Then, ethanol is added to decompose unreacted phenylmagnesium bromide. Toluene and 1 N hydrochloric acid were added and stirred.

The mixed liquid is transferred to a separating funnel, and the water layer is separated. After the toluene layer is washed with water, the toluene is distilled off to obtain an α-olefin compound having a phenyl-substituted end.

The above reaction can be carried out in the same manner on a compound wherein R is a phenyl group having a substituent.

The Second and Third Steps

The steps are carried out in the same manner as in the case where the above R is an alkoxy group.

(2) Method for Forming an Organic Thin Film

A method for forming an organic thin film in the present invention preferably uses, but not particularly limited to, at least one method selected from the group consisting of vacuum deposition, liquid phase deposition, chemical vapor deposition, the Langmuir method, sputtering, dipping (immersion), spray coating, spin coating, roller coating, brushing, and screen printing.

The vapor deposition is a method in which a thin film substance (a substance to be a material of a thin film) is heated in vacuum to be vaporized, and the vapor is condensed and solidified on a base material surface at a temperature lower than the vaporization temperature to thereby form a thin film. Alternatively, the liquid phase deposition is a method in which a thin film substance is dissolved in a solvent at a high temperature so as to be in a supersaturation state, and a thin film is formed by bringing the solution while cooled into contact with a base material to allow crystals of the thin film substance to deposit on the base material. The chemical vapor deposition is a method in which a thin film substance is converted into radicals to increase its reactivity by energizing a gas containing the thin film substance with heat or light, or by plasmatizing the gas with radio frequency, and the radicals are allowed to adsorb on a base material surface to thereby form a thin film. The Langmuir method is a method in which monolayers formed on a water surface are transferred one by one to a solid base material surface to thereby accumulate molecular layers on the base material. The sputtering is a method in which, using a property that accelerated ion irradiation on a solid thin film substance (target substance) allows atoms and molecules to be emitted out on the surface of the target substance, the target substance is allowed to attach to a base material surface to thereby form a thin film. The dipping is a method in which a base material is immersed in a solution containing a thin film substance to form a thin film on a base material surface. The spray coating is a method in which a solution containing a thin film substance is sprayed on a base material to form a thin film on a base material surface. The spin coating is a method in which a solution of a thin film substance is placed on a base material mounted on a disc, the disc is rotated to allow the solution to be a homogeneous liquid film, and the film is calcined to thereby form a thin film. The roller coating is a method in which a solution of an organic thin film substance is applied on a base material surface with a roller in a thin layer to thereby form a thin film. The brushing is a method in which a solution of an organic thin film substance is applied on a base material surface with a brush in a thin layer to thereby form a thin film. The screen printing is a method in which a thin film substance (paste) is placed on a screen (fabric) stretched on a frame and sliding is carried out under pressure to thereby form a thin film on the base material.

Alternatively, in the case of the dipping, the period during which a base material is immersed in an organic solvent solution depends on types of the base material and the like and can range from 5 minutes to 24 hours, is preferably from 5 minutes to 10 hours, although it is not always the case.

In the present invention, a method for forming an organic thin film is preferably a forming method which comprises bringing the base material into contact with an organic thin film forming solution containing an organosilicon compound represented by formula (I) and a compound that can interact with the organosilicon compound using the dipping.

Specifically, the method has the steps of:

(A) mixing the organosilicon compound, a compound that can interact with the organosilicon compound, and water in an organic solvent to prepare an organic thin film forming solution, and (B) bringing the obtained organic thin film forming solution into contact with a substrate.

This makes it possible to form a denser organic thin film having fewer impurities more quickly.

1) Method for Preparing an Organic Thin Film Forming Solution

Examples of a method for preparing an organic thin film forming solution used in the dipping include the methods described in WO 03/076064, WO 2004/091810, WO 2006/009292, WO 2009/104424, and WO 2008/059840, and also include a method involving mixing a) an organosilicon compound represented by formula (I)

b) an organic thin film forming aid obtained by mixing a metal surfactant having at least one hydrolyzable group (that may be identical to the organosilicon compound represented by formula (I)) and a compound that can interact with the metal surfactant and the organosilicon compound in an organic solvent, and c) water, and then diluting the mixture with an organic solvent.

As an alternative, in the case where the metal surfactant and the organosilicon compound are identical, it is also possible, without preparing an organic thin film forming aid first, to mix an organosilicon compound represented by formula (I), a compound that can interact with the organosilicon compound, and water and then, to dilute the mixture with an organic solvent.

Examples of the metal surfactant used in the aid herein include an organic metal compound represented by formula (II)

$$R^1{}_{n^1}MX^1{}_{m-n^1} \quad (II)$$

[wherein, $R^1$ represents a hydrocarbon group having 1 to 30 carbon atoms that optionally has a substituent, a halogenated hydrocarbon group having 1 to 30 carbon atoms that optionally has a substituent, a hydrocarbon group having 1 to 30 carbon atoms comprising a linking group, or a halogenated hydrocarbon group having 1 to 30 carbon atoms comprising a linking group, M represents at least one metal atom selected from the group consisting of a silicon atom, a germanium atom, a tin atom, a titanium atom, and a zirconium atom, $X^1$ represents a hydroxyl group or a hydrolyzable group, and m represents the atomic valence of M; $n^1$ represents a positive integer from 1 to (m−1), when $n^1$ is 2 or more, each $R^1$ may be identical or different, and when (m−$n^1$) is 2 or more, each $X^1$ may be identical or different] or an oligomer thereof.

Examples of the hydrocarbon group in the hydrocarbon group having 1 to 30 carbon atoms that optionally has a substituent include an alkyl group having 1 to 30 carbon atoms, such as a methyl group, an ethyl group, a n-propyl group, an isopropyl group, a n-butyl group, an isobutyl group, a sec-butyl group, a t-butyl group, a n-pentyl group, an isopentyl group, a neopentyl group, a t-pentyl group, a n-hexyl group, an isohexyl group, a n-heptyl group, a n-octyl group, and a n-decyl group; an alkenyl group having 1 to 30 carbon atoms; and an aryl group such as a phenyl group and a naphthyl group.

Examples of the halogenated hydrocarbon group in the halogenated hydrocarbon group having 1 to 30 carbon atoms that optionally has a substituent include halogenated alkyl groups having 1 to 30 carbon atoms, a halogenated alkenyl group having 1 to 30 carbon atoms, and a halogenated aryl group. Examples of the halogen atom include a fluorine atom, a chlorine atom, and a bromine atom, and a fluorine atom is preferred. Specifically, examples include a group in which one or more hydrogen atoms in the hydrocarbon group exemplified above are substituted with a halogen atom, such as a fluorine atom, a chlorine atom, or a bromine atom.

Examples of the substituent in the hydrocarbon group having 1 to 30 carbon atoms that optionally has a substituent or the halogenated hydrocarbon group having 1 to 30 carbon atoms that optionally has a substituent include a carboxyl group; an amide group; an imide group; an ester group; an alkoxy group such as a methoxy group and an ethoxy group; or a hydroxyl group. The number of these substituents is preferably 0 to 3.

Examples of the hydrocarbon group in the hydrocarbon group having 1 to 30 carbon atoms that comprises a linking group specifically include those similar to those exemplified as the hydrocarbon group in the hydrocarbon group having 1 to 30 carbon atoms that optionally has a substituent.

Additionally, examples of the halogenated hydrocarbon group in the halogenated hydrocarbon group having 1 to 30 carbon atoms that comprises a linking group specifically include those similar to those exemplified as the halogenated hydrocarbon group in the halogenated hydrocarbon group having 1 to 30 carbon atoms that optionally has a substituent.

The linking group is preferably present between carbon-carbon bonds of the hydrocarbon group or halogenated hydrocarbon group, or between a carbon of the hydrocarbon group and a metal atom M described below.

Specific examples of the linking group include —O—, —S—, —SO$_2$—, —CO—, —C(=O)O—, or —C(=O)NR$^2$— (wherein R$^2$ represents a hydrogen atom; or an alkyl group such as a methyl group, an ethyl group, a n-propyl group, and an isopropyl group).

(Preparation of an Organic Thin Film Forming Aid)

An "organic thin film forming aid" can be obtained by mixing the metal surfactant and a compound that can interact with the metal surfactant and the organosilicon compound.

An organic thin film forming aid can be prepared more specifically by mixing a metal surfactant and a compound that can interact with the metal surfactant and the organosilicon compound in an organic solvent with or without addition of water.

In the present invention, the organic thin film forming aid contains 0.5 to 80% by weight, preferably 5 to 50% by weight of the metal surfactant.

When the compound that can interact with the metal surfactant and the organosilicon compound is at least one selected from the group of consisting of metal hydroxides, metal alkoxides, partial hydrolysis products of metal alkoxides, and silanol condensation catalysts, the compound is contained in an amount of 0.1 ppm to 5% by weight, preferably 10 ppm to 2% by weight in terms of metal. However, in the case of an acid catalyst, the compound is contained in an amount of 0.001 mmol to 1 mol, preferably 0.01 mmol to 10 mmol relative to the total 1 mol of the metal surfactant and the organosilicon compound represented by formula (I).

The amount of water used is 0.01 to 5.0 mol, preferably 0.1 to 2.0 mol relative to 1 mol of the metal surfactant. However, water is not necessarily added. It is also possible to use only the moisture absorbed from air and the moisture contained in the raw materials.

The reaction temperature ranges from 0 to 100° C., and the reaction time ranges from 1 hour to 10 days.

Examples of the method carried out by adding water when the metal surfactant is mixed with a compound that can interact with the metal surfactant in an organic solvent specifically include (i) a method in which water is added to an organic solvent solution containing a metal surfactant and a compound that can interact with the metal surfactant, and (ii) a method in which, to an organic solvent solution containing a metal surfactant and water, a compound that can interact with the metal surfactant is added. The compound that can interact with the metal surfactant is generally used in the state of an organic solvent containing water.

Examples of the organic solvent used for preparing the organic thin film forming aid preferably include hydrocarbon solvents, fluorocarbon solvents, and silicone solvents. Of these, solvents having a boiling point of 100 to 250° C. are more preferred.

Examples specifically include a hydrocarbon solvent such as n-hexane, cyclohexane, benzene, toluene, xylene, petroleum naphtha, solvent naphtha, petroleum ether, petroleum benzin, isoparaffin, normal paraffin, decalin, industrial gasoline, kerosene, and ligroin; a chlorofluorocarbon solvent such as CBr$_2$ClCF$_3$, CClF$_2$CF$_2$CCl$_3$, CClF$_2$CF$_2$CHFCl, CF$_3$CF$_2$CHCl$_2$, CF$_3$CBrFCBrF$_2$, CClF$_2$CClFCF$_2$CCl$_3$, Cl(CF$_2$CFCl)$_2$Cl, Cl(CF$_2$CFCl)$_2$CF$_2$CCl$_3$, Cl(CF$_2$CFCl)$_3$Cl, a fluorocarbon solvent such as Fluorinert (a product of 3M Corporation) and Afrude (a product of Asahi Glass Co., Ltd.); a silicone solvent such as dimethylsilicone, phenylsilicone, alkyl-modified silicone, and polyether silicone; a ketone solvent such as acetone, methyl ethyl ketone, methyl isobutyl ketone, diethyl ketone, dipropyl ketone, and dibutyl ketone; and an ethylene glycol ether solvent such as ethylene glycol dimethyl ether, ethylene glycol diethyl ether, ethylene glycol dibutyl ether, diethylene glycol diethyl ether, and diethylene glycol dibutyl ether. These solvents can be used singly or in combinations of two or more.

Alternatively, in order to suppress an abrupt reaction, the water to be added in the method (i) and the compound that can interact with the metal surfactant to be added in the method (ii) have been preferably diluted with an organic solvent and the like.

(Compound that can Interact with the Metal Surfactant and the Organosilicon Compound Represented by Formula (I))

A compound that can interact with the metal surfactant and the organosilicon compound represented by formula (I) means a compound having an effect of activating a hydrolyzable group or a hydroxyl group of the metal surfactant and the organosilicon compound by forming a chemical bond such as a coordinate bond and a hydrogen bond with a hydrolyzable group portion or a hydroxyl group portion to accelerate condensation of the metal surfactant and the organosilicon compound.

The compound that can interact with the metal surfactant and the organosilicon compound represented by formula (I) is not particularly limited provided that it has the aforementioned effect, and at least one compound selected from the group of consisting of
metal oxides;
metal hydroxides;
metal alkoxides;
partial hydrolysis products of metal alkoxides;
hydrolysis products obtained by treating metal alkoxides with two-fold or more equivalent of water;
chelated or coordinated metal compounds; and
silanol condensation catalysts
is particularly preferred. Metal alkoxides and partial hydrolysis products of metal alkoxides are more preferred.

The metal in metal oxides; metal hydroxides; metal alkoxides; chelated or coordinated metal compounds; partial hydrolysis products of metal alkoxides; hydrolysis products obtained by treating metal alkoxides with two-fold or more equivalent of water; and silanol condensation catalysts is, but not particularly limited to, preferably at least one selected from the group consisting of titanium, zirconium, aluminum, silicon, germanium, indium, tin, tantalum, zinc, tungsten, and lead, is more preferably titanium, zirconium, aluminum or silicon, and titanium or silicon is particularly preferred.

a) Metal Oxide

Metal oxides can be used in any state such as sol, gel, and solid states. Methods for producing a gel or sol are not particularly limited. In the case of a silica sol, examples of the method include a method in which a sodium silicate solution is subjected to cation exchange and a method in which a silicon alkoxide is hydrolyzed. A sol stably dispersed in an organic solvent is particularly preferred. Additionally, the sol has a particle size preferably in the range from 10 to 100 nm, more preferably in the range from 10 to 20 nm. The sal shape is not particularly limited, and sols having any shape such as spherical or elongated shapes can be used.

Specific examples of the metal oxide include methanol silica sol, IPA-ST, IPA-ST-UP, IPA-ST-ZL, NPC-ST-30, DMAC-ST, MEK-ST, MIBK-ST, XBA-ST, and PMA-ST (all of which are product names of organosilica sols manufactured by Nissan Chemical Industries, Ltd.).

b) Metal Hydroxide

Metal hydroxides include those produced by any production method provided that the product is a hydroxide of a metal. Examples of the method for producing a metal hydroxide include a method in which a metal alkoxide described below is hydrolyzed and a method in which a metal salt is allowed to react with a metal hydroxide. Commercially available metal hydroxides may also be purified and used as required.

c) Metal Alkoxide

The number of carbon atoms in the alkoxy group of a metal alkoxide is not particularly limited. However, from the viewpoints of the concentration of the oxide contained, ease of eliminating an organic matter, availability, and the like, the number of carbon atoms is preferably 1 to 4. Specific examples of the metal alkoxide used in the present invention include a silicon alkoxide such as $Si(OCH_3)_4$, $Si(OC_2H_5)_4$, $Si(OC_3H_7\text{-i})_4$, and $Si(OC_4H_9\text{-t})_4$; a titanium alkoxide such as $Ti(OCH_3)_4$, $Ti(OC_2H_5)_4$, $Ti(OC_3H_7\text{-i})_4$, and $Ti(OC_4H_9)_4$; tetrakistrialkylsiloxy titanium such as $Ti[OSi(CH_3)_3]_4$ and $Ti[OSi(C_2H_5)_3]_4$; a zirconium alkoxide such as $Zr(OCH_3)_4$, $Zr(OC_2H_5)_4$, $Zr(OC_3H_7)_4$, and $Zr(OC_4H_9)_4$; an aluminum alkoxide such as $Al(OCH_3)_4$, $Al(OC_2H_5)_4$, $Al(OC_3H_7\text{-i})_4$, and $Al(OC_4H_9)_3$; a germanium alkoxide such as $Ge(OC_2H_5)_4$; an indium alkoxide such as $In(OCH_3)_3$, $In(OC_2H_5)_3$, $In(OC_3H_7\text{-i})_3$, and $In(OC_4H_9)_3$; a tin alkoxide such as $Sn(OCH_3)_4$, $Sn(OC_2H_5)_4$, $Sn(OC_3H_7\text{-i})_4$, and $Sn(OC_4H_9)_4$; a tantalum alkoxide such as $Ta(OCH_3)_5$, $Ta(OC_2H_5)_5$, $Ta(OC_3H_7\text{-i})_5$, and $Ta(OC_4H_9)_5$; a tungsten alkoxide such as $W(OCH_3)_6$, $W(OC_2H_5)_6$, $W(OC_3H_7\text{-i})_6$, and $W(OC_4H_9)_6$; a zinc alkoxide such as $Zn(OC_2H_5)_2$; and a lead alkoxide such as $Pb(OC_4H_9)_4$. These metal alkoxides can be used singly, or in combinations of two or more.

Furthermore, in the present invention, a composite alkoxide obtained by reacting two or more metal alkoxides, a composite alkoxide obtained by reacting one or more metal alkoxides with one or more metal salts, or a combination of these can also be used as the metal alkoxide.

Examples of composite alkoxides obtained by reacting two or more metal alkoxides include a composite alkoxide obtained by reacting an alkali metal or alkaline earth metal alkoxide with a transition metal alkoxide, and a composite alkoxide obtained as complex salts by combining elements from the group 3B.

Specific examples include $BaTi(OR)_6$, $SrTi(OR)_6$, $BaZr(OR)_6$, $SrZr(OR)_6$, $LiNb(OR)_6$, $LiTa(OR)_6$, and a combination thereof, as well as products of reaction between a silicon alkoxide and an aforementioned metal alkoxide such as $LiVO(OR)_4$, $MgAl_2(OR)_9$, $(RO)_3SiOAl(OR')_2$, $(RO)_3SiOTi(OR')_3$, $(RO)_3SiOZr(OR')_3$, $(RO)_3SiOB(OR')_2$, $(RO)_3SiONb(OR')_4$, and $(RO)_3SiOTa(OR')_4$ and a condensation-polymerization product thereof. R and R' herein each represent an alkyl group and the like.

Examples of composite alkoxide obtained by reacting one or more metal alkoxides with one or more metal salts include a compound obtained by reacting a metal salt with a metal alkoxide.

Examples of the metal salt include chloride, nitrate, sulfate, acetate, formate, and oxalate of a metal, and examples of the metal alkoxide include the metal alkoxide as aforementioned.

d) Partial Hydrolysis Products of Metal Alkoxides

Partial hydrolysis products of metal alkoxides are products obtained prior to complete hydrolysis of the metal alkoxide, and examples include a metal oxide sol precursor, or that in an oligomer state.

Specific examples of the partial hydrolysis product of the metal alkoxide preferably include a dispersoid that has stable dispersibility in an organic solvent without aggregating, in the absence of at least one selected from the group consisting of acids, bases, and dispersion stabilizers. In this case, the dispersoid refers to fine particles dispersed in a dispersion system, and examples specifically include colloidal particles. The "stably dispersed state without aggregating" herein means a state in which the hydrolysis product dispersoid do not aggregate and is not heterogeneously separated in the organic solvent in the absence of acids, bases, and/or dispersion stabilizers, but rather preferably means a transparent and homogeneous state. "Transparent" means that a state in which the transmittance of visible light is high, and specifically, refers to a state in which the transmittance is preferably in a range from 80 to 100%, wherein the transmittance is represented by the spectral transmittance measured under a condition of a light wavelength at 550 nm, when the concentration by oxide conversion of the dispersoid is set to 0.5% by weight, a quartz cell with an optical path length of 1 cm is used, and an organic solvent is used as a control sample. The particle size of the hydrolysis product dispersoid is not particularly limited. However, in order to achieve a high transmittance of visible light, the particle size is preferably in the range from 1 to 100 nm, more preferably in the range from 1 to 50 nm, still more preferably in the range from 1 to 10 nm. Additionally, acids, bases, and dispersion stabilizers are described below.

Examples of the method for producing a partial hydrolysis product of a metal alkoxide preferably include a method in which a metal alkoxide exemplified above is hydrolyzed in an organic solvent in the absence of acids, bases, and/or dispersion stabilizers, using from 0.5 to less than 2.0 fold mol of water relative to the metal alkoxide at a temperature in the range from −100° C. to the reflux temperature of the organic solvent.

Examples of the method specifically include
(i) a method in which 0.5 to less than 1.0 fold mol of water relative to the metal alkoxide is added in an organic solvent in the absence of acids, bases, and/or dispersion stabilizers,
(ii) a method in which 1.0 to less than 2.0 fold mol of water relative to the metal alkoxide is added in an organic solvent in the absence of acids, bases, and/or dispersion stabilizers at a temperature equal to or less than that at which hydrolysis is initiated, or at 0° C. or less, preferably at a temperature in the range from −50 to −100° C., and
(iii) a method in which 0.5 to less than 2.0 fold mol of water relative to the metal alkoxide is added in an organic solvent at room temperature in the absence of acids, bases, and/or dispersion stabilizers, but with the rate of the hydrolysis controlled, for example, by a method of controlling the rate of addition of the water, or lowering the concentration of water to be added by dilution with a water-soluble solvent or the like.

In the method (i) described above, after the treatment is carried out with a predetermined amount of water at an arbitrary temperature, the reaction can be carried out with water further added under a temperature condition of a temperature equal to or less than that at which hydrolysis is initiated, or of −20° C. or less. The reaction between the metal alkoxide and water can be carried out by mixing the metal alkoxide and water directly without using an organic solvent, but the reaction is preferably carried out in an organic solvent. Specifically, the reaction can be carried out either by a method in which water diluted with the organic solvent is added to an organic solvent solution of the metal alkoxide, or a method in which the metal alkoxide or an organic solvent solution thereof is added to an organic solvent containing water suspended or dissolved therein, but the former method, in which the water is added afterwards, is preferred. The water used is not particularly limited provided that it is neutral, but pure water or distilled water is preferably used. The amount of water used is not particularly limited provided that it satisfies the range predetermined above, and the amount can be arbitrarily selected depending on a dispersoid having the intended properties.

The concentration of the metal alkoxide in the organic solvent is not particularly limited provided that the concentration is in a range that provides fluidity to enable suppression of rapid heat generation and stirring, but the concentration in the range from 5 to 30% by weight is preferred.

In the method (i) described above, the reaction temperature for the reaction between the metal alkoxide and water is not particularly limited, but the temperature can be in the range from −100 to +100° C. and is preferably in the range from −20° C. to the boiling point of either the organic solvent used or the alcohol eliminated by hydrolysis.

In the method (ii) described above, the temperature at which water is added varies depending on the stability of the metal alkoxide. Although the temperature is not particularly limited provided that the temperature is either not higher than the hydrolysis initiation temperature or not higher than 0° C., water is added to the metal alkoxide preferably at a temperature in the range from −50° C. to −100° C., depending on the type of the metal alkoxide. Alternatively, after addition of water at a low temperature and aging for a certain period, it is also possible to carry out hydrolysis at a temperature in the range from room temperature to the reflux temperature of the solvent used, and then, to further carry out a dehydration condensation reaction.

In the method (iii) described above, the reaction between the metal alkoxide and water can be carried out in a temperature range that can be cooled without using special cooling equipment, for example, a temperature range from 0° C. to room temperature, by controlling the hydrolysis rate by means of factors other than temperature, such as by controlling the rate at which water is added. After aging for a certain period, it is also possible to carry out hydrolysis at a temperature in the range from room temperature to the reflux temperature of the solvent used, and then, to further carry out a dehydration condensation reaction.

The organic solvent used is preferably capable of dispersing the hydrolysis product of the metal alkoxide as a dispersoid. Since the reaction for treating the metal surfactant with water can be carried out at low temperatures, a solvent that has high water solubility and does not freeze at low temperatures is more preferred. Specific examples of the organic solvent used include an alcohol solvent such as methanol, ethanol, and isopropanol; a halogenated hydrocarbon solvent such as methylene chloride, chloroform, and chlorobenzene; a hydrocarbon solvent such as hexane, cyclohexane, benzene, toluene, and xylene; an ether solvent such as tetrahydrofuran, diethyl ether, and dioxane; a ketone solvent such as acetone, methyl ethyl ketone, and methyl isobutyl ketone; an amide solvent such as dimethylformamide and N-methylpyrrolidone; a sulfoxide solvent such as dimethylsulfoxide; and silicone such as methylpolysiloxane, octamethylcyclotetrasiloxane, decamethylcyclopentasiloxane, and methylphenylpolysiloxane (Japanese unexamined Patent Application Publication No. 9-208438 and the like). These solvents can be used singly, or as a mixture of two or more.

In the case of being used as a mixed solvent, a combination of a hydrocarbon solvent such as toluene and xylene and a lower alcohol solvent such as methanol, ethanol, isopropanol, and t-butanol is preferred. As the lower alcohol solvent in such a case, a secondary or higher alcohol solvent such as isopropanol and t-butanol is more preferably used. The mixing ratio of the mixed solvent is not particularly limited, but a hydrocarbon solvent and a lower alcohol solvent are preferably used in a volume ratio in the range from 99/1 to 50/50.

Alternatively, in hydrolysis reaction of the metal alkoxide with water, an acid, a base, or a dispersion stabilizer may be added. The acid and base are not particularly limited, provided that they function as a deflocculant for re-dispersing any precipitate that settles out, as a catalyst for the hydrolysis and dehydration condensation of the metal alkoxide to produce a dispersoid of colloidal particles or the like, or as a dispersing agent for the dispersoid formed.

The acid or base in such a case are not particularly limited provided that it functions as a deflocculant for re-dispersing any precipitate produced by flocculation, also as mentioned above, as a catalyst for the hydrolysis and dehydration condensation of the metal alkoxide or the like to produce a dispersoid of colloidal particles or the like, and as a dispersing agent for the dispersoid formed.

Examples of the acid used include a mineral acid such as hydrochloric acid, nitric acid, boric acid, and fluoroboric acid; an organic acid such as acetic acid, formic acid, oxalic acid, carbonic acid, trifluoroacetic acid, p-toluenesulfonic acid, and methanesulfonic acid; and a photoacid generator that generates acid on light irradiation such as diphenyliodonium hexafluorophosphate and triphenylphosphonium hexafluorophosphate.

Examples of the base used include triethanolamine, triethylamine, 1,8-diazabicyclo[5.4.0]-7-undecene, ammonia, dimethylformamide, and phosphine.

A dispersion stabilizer is an agent having an effect of stably dispersing a dispersoid in a dispersion medium. Examples of the dispersion stabilizer include a coagulation inhibitor such as a deflocculant, a protective colloid, and a surfactant. Specific examples include a polyvalent carboxylic acid such as glycolic acid, gluconic acid, lactic acid, tartaric acid, citric acid, malic acid, and succinic acid; a hydroxycarboxylic acid; a phosphoric acid such as pyrophosphoric acid and tripolyphosphoric acid; a polydentate ligand compound that exhibits a powerful chelating capability relative to metal atoms such as acetylacetone, methyl acetoacetate, ethyl acetoacetate, n-propyl acetoacetate, isopropyl acetoacetate, n-butyl acetoacetate, sec-butyl acetoacetate, t-butyl acetoacetate, 2,4-hexanedione, 2,4-heptanedione, 3,5-heptanedione, 2,4-octanedione, 2,4-nonanedione, and 5-methylhexanedione; an aliphatic amine polyesteramine and a hydrostearic acid polyesteramine such as Solsperse 3000, 9000, 17000, 20000, and 24000 (all manufactured by Zeneca PLC), and Disperbyk-161, -162, -163, and -164 (all manufactured by BYK-Chemie GmbH); and a silicone compound such as a dimethylpolysiloxane-methyl(polysiloxyalkylene)siloxane copolymer, trimethylsiloxysilicic acid, carboxy-modified silicone oil, and amine-modified silicone (Japanese unexamined Patent Application Publication No. 9-208438, Japanese unexamined Patent Application Publication No. 2000-53421, and the like).

e) Hydrolysis Product Obtained by Hydrolyzing a Metal Alkoxide with a Two-Fold or More Equivalent of Water A metal alkoxide hydrolysis product used in the present invention is a product obtained by hydrolyzing a metal alkoxide with a two-fold or more equivalent of water. The hydrolysis product may be obtained either by hydrolyzing a metal alkoxide with a two-fold or more equivalent of water, or by partially hydrolyzing a metal alkoxide with less than a two-fold equivalent of water relative to the metal alkoxide to obtain a partial hydrolysis product of the metal alkoxide, and then further hydrolyzing the partial hydrolysis product with a predetermined amount of water (water in an amount that achieves a two-fold or more equivalent of water relative to the metal alkoxide, when totaled to the amount of water used in the above partial hydrolysis).

The reaction between the metal alkoxide and water may be carried out by directly mixing the metal alkoxide and water without using an organic solvent, or by reacting the metal alkoxide and water in an organic solvent, but the metal alkoxide and water are preferably reacted in an organic solvent. The water used herein is not particularly limited provided that it is neutral, but from the viewpoints of minimizing impurities and achieving a denser organic thin film, pure water, distilled water, or ion exchange water is preferably used. The amount of water used is preferably a two-fold or more equivalent, more preferably a 2 to 8-fold equivalent, still more preferably a 3 to 5-fold equivalent relative to the metal alkoxide.

Examples of the methods in which a metal alkoxide and water are reacted in an organic solvent include (1) a method in which either water, or water diluted with an organic solvent is added to an organic solvent solution of the metal alkoxide, and (2) a method in which the metal alkoxide or an organic solvent solution thereof is added to an organic solvent containing water suspended or dissolved therein. In this case, the concentration of the metal alkoxide in the organic solvent is not particularly limited provided that the concentration is in a range where a rapid exothermic is suppressed and fluidity to enable stirring is provided, but the concentration in the range from 5 to 30% by weight relative to the whole amount of the reaction solution is preferred.

The organic solvents used are not particularly limited. Of the organic solvents, those capable of dispersing the hydrolysis product of the metal alkoxide as a dispersoid are preferred. Specific examples include the same organic solvents as those listed in relation to the partial hydrolysis products of metal alkoxides. Furthermore, in addition to the organic solvent, the water, acids, bases, dispersion stabilizers, or the like used in the partial hydrolysis products can be used in the hydrolysis product as well. The hydrolysis reaction temperature of the metal alkoxide varies depending on the reactivity, stability, and the like of the metal alkoxide used, but can be in the range from −100° C. to the reflux temperature of the organic solvent, preferably in the range from −100° C. to −20° C. After water is added at a low temperature and the mixture is allowed to age for a certain period, it is also possible to increase the temperature of the reaction liquid from room temperature to the reflux temperature of the solvent used to thereby further carry out hydrolysis and dehydration condensation reaction.

f) Chelated or Coordinated Metal Compound

Chelated or coordinated metal compounds can be prepared by adding, to a solution of a metal compound, a chelating agent or coordination compound capable of forming a complex with the metal of the metal compound. The chelating agents or coordination compounds used are not particularly limited provided that they are capable of chelating or coordinating the metal of metal hydroxides, metal alkoxides, or hydrolysis products obtained by treating metal alkoxides with water to thereby form a complex.

Specific examples of the chelating agent or coordination compound include a saturated aliphatic carboxylic acid such as acetic acid, propionic acid, butyric acid, valeric acid, lauric acid, myristic acid, palmitic acid, and stearic acid; a saturated aliphatic dicarboxylic acid such as oxalic acid, malonic acid, succinic acid, glutaric acid, adipic acid, pimelic acid, suberic acid, azelaic acid, and sebacic acid; an unsaturated carboxylic acid such as acrylic acid, methacrylic acid, crotonic acid, aleic acid, and maleic acid; an aromatic carboxylic acid such as benzoic acid, toluic acid, and phthalic acid; a halogenocarboxylic acid such as chloroacetic acid and trifluoroacetic acid; a β-diketone such as acetylacetone, benzoylacetone, and hexafluoroacetylacetone; a β-ketoester such as methyl acetoacetate and ethyl acetoacetate; and a heterocyclic compound such as tetrahydrofuran, furan, furancarboxylic acid, thiophene, thiophenecarboxylic acid, pyridine, nicotinic acid, and isonicotinic acid. These can be used singly, or in combinations of two or more.

The amount of the chelating agent or coordination compound added is preferably in the range from 0.1 to 10 fold mol, more preferably from 0.3 to 2 fold mol, still more preferably from 0.5 to 1.2 fold mol per mol of the metal of the metal hydroxide, metal alkoxide, or hydrolysis product obtained by treating a metal alkoxide with water.

Following addition of the chelating agent or coordination compound, a solution of the metal complex can be obtained by sufficiently stirring the whole volume. The stirring temperature is not particularly limited, but is preferably in a temperature range from 0° C. to the boiling point of the solvent used. The stirring time is not particularly limited, but is preferably in a range from several minutes to several hours. The chelated or coordinated metal compound that has been isolated can be used, or a solution of the chelated or coordinated metal compound obtained by addition of the chelating agent or coordination compound to the solution of the metal compound can be used. Alternatively, a solution of the chelated or coordinated metal compounds prepared can be stored.

g) Silanol Condensation Catalyst

Examples of the silanol condensation catalyst include a carboxylate metal salt, a carboxylate ester metal salt, a carboxylate metal salt polymer, a carboxylate metal salt chelate, a titanate ester, and a titanate ester chelate. Examples specifically include stannous acetate, dibutyltin dilaurate, dibutyltin dioctate, dibutyltin diacetate, dioctyltin dilaurate, dioctyltin dioctate, dioctyltin diacetate, stannous dioctanoate, lead naphthenate, cobalt naphthenate, iron 2-ethylhexanoate, dioctyltin bisoctylthioglycolate, dioctyltin maleate, dibutyltin maleate polymer, dimethyltin mercaptopropionate polymer, dibutyltin bisacetylacetate, dioctyltin bisacetyllaurate, titanium tetraethoxide, titanium tetrabutoxide, titanium tetraisopropoxide, and titanium bis(acetylacetonyl)dipropoxide.

(Preparation of "Hydroxyl Group-Containing Solution" Before Dilution with an Organic Solvent)

A "hydroxyl group-containing solution" can be obtained from the organic thin film forming aid and the organosilicon compound. More specifically, mixing and stirring of the organosilicon compound, the organic thin film forming aid, an organic solvent, and water causes hydrolysis to thereby produce a hydroxyl group-containing compound, from which a hydroxyl group-containing solution can be obtained.

In that case, the total amount of the metal surfactant and the organosilicon compound used is 0.1 to 80% by weight, preferably 0.5 to 50% by weight based on the entire hydroxyl group-containing solution.

Alternatively, the ratio of the metal surfactant and the organosilicon compound used is not particularly limited, but is typically 1:10 to 50,000, preferably 1:150 to 20,000 by weight.

As an alternative, in the case where an organosilicon compound represented by formula (I), a compound that can interact with the organosilicon compound, and water are mixed without preparing an organic thin film forming aid, mixing is carried out such that the amount of the organosilicon compound reaches 0.1% by weight to 80% by weight. Then, hydrolysis is carried out to produce a hydroxyl group-containing compound, from which a hydroxyl group-containing solution is prepared.

Organic solvents used for preparing a hydroxyl group-containing solution of the present invention are preferably hydrocarbon solutions, fluorocarbon solvents, and silicone solvents. Of these, solvents having a boiling point of 100 to 250° C. are more preferred. Specifically, it is possible to use solvents similar to the hydrocarbon solvents, fluorocarbon solvents, and silicone solvents listed as those which can be used for preparation of the organic thin film forming aid.

The amount of water used for preparing a hydroxyl group-containing solution of the present invention can be determined as appropriate, depending on types of the organosilicon compound and the organic thin film forming aid used and the substrate on which application is made and the like.

The stirring temperature for the mixture of the organosilicon compound, organic solvent, organic thin film forming aid, and water is typically from −100° C. to +100° C., preferably from −20° C. to +50° C. The stirring time is typically from 1 hour to 100 days.

Alternatively, in this case, ultrasonic treatment is preferably carried out in order to obtain a homogeneous organic thin film forming solution.

In some cases, a precipitate containing metal oxide and the like may develop in the hydroxyl group-containing solution prepared. Impurities such as the precipitate are preferably removed at this point to obtain a dense monolayer organic thin film having no impurities. Precipitates can be removed easily by an operation such as filtration or decantation.

In the present invention, a hydroxyl group-containing solution of which water content is adjusted or maintained so as to be in the predetermined range is used. The water content is preferably in a range so as not to cause problems such as inhibition of chemical adsorption on the substrate surface, inability to produce a dense monolayer, a loss of the amount of the metal surfactant effectively used, or deactivation of the catalyst. Alternatively, in the case where the substrate is brought into contact with the solution by dipping, it is possible to accelerate and activate formation of a substrate surface or film so as to form a dense and homogeneous organic thin film at a time as well as across the entire surface of the substrate with which the solution has contacted within a contact time of 10 minutes, preferably 5 minutes.

(Preparation of an Organic Thin Film Forming Solution)

When the hydrolysis reaction progresses to increase the hydroxyl group-containing compound and allow the concentration of the hydroxyl group to reach equilibrium, the solution is diluted 1.5 to 200 folds, preferably 2 to 100 folds, more preferably 10 to 50 folds with an organic solvent to thereby prepare the ultimate organic thin film forming solution. The time required for the concentration of the hydroxyl group to reach equilibrium is, but not particularly limited to, 1 hour to 1 month, preferably 1 week to 2 weeks.

It should be noted that the state in which the concentration of the hydroxyl group reaches equilibrium herein can be confirmed by measuring the peak of the position corresponding to monosilanol over time with reverse phase HPLC using a metal surfactant, for example, octadecyl trimethoxysilane before hydrolysis as a standard.

When the hydrolysis reaction progresses to increase the hydroxyl group-containing compound and allow the concentration of the hydroxyl group to reach equilibrium, the conversion ratio from the organosilicon compound added to the hydroxyl group-containing compound is 5 to 50% by weight, preferably 8% by weight to 30% by weight.

The added total amount of the metal surfactant and the organosilicon compound in the entire organic thin film forming solution after dilution is 0.05% by weight to 50% by weight, preferably 0.1% by weight to 10% by weight. The amount of a hydroxyl group-containing compound produced with the progress of the hydrolysis reaction is 20 ppm to 6% by weight, preferably 50 ppm to 1% by weight. When the compound that can interact with the metal surfactant and the organosilicon compound is at least one selected from the group consisting of metal hydroxides, metal alkoxides, partial hydrolysis products of metal alkoxides, and silanol condensation catalysts, the amount of the compound is 0.01 ppm to 8 ppm, preferably 0.03 ppm to 2 ppm in terms of metal.

Alternatively, the water content of the organic thin film forming solution is 10 ppm to 2000 ppm, and may be as small as 10 ppm to less than 50 ppm.

It should be noted that the water content shown herein is a value measured on a portion collected from the organic solvent solution by the Karl Fischer method. Provided that the value is measured with a device employing the methodology principle, the measuring device is not particularly limited.

(Preparation of an Organic Thin Film)

The step of bringing the organic thin film forming solution into contact with a base material may be carried out for a long period at a time, or may be carried out for a short period at many times. Alternatively, ultrasonic waves may be used in order to accelerate formation of an organic thin film.

The temperature of the organic thin film forming solution in bringing the organic thin film forming solution into contact with a base material is not particularly limited provided that the temperature is in a range that allows the solution to maintain its stability, but the temperature is typically in the range from room temperature to the reflux temperature of the solvent used for preparation of the solution. In order to bring the organic thin film forming solution to a temperature suitable for contact, the organic thin film forming solution, the base material itself, or both of them may be heated.

A step of washing the base material with an organic solvent may be included after an organic thin film of the present invention is formed. With such a washing step, excess reagents or impurities adhered on the surface of the organic thin film formed are removed. Provision of such a washing step also enables the thickness of the organic thin film formed on the base material surface to be controlled.

The organic solvent used herein is not particularly limited, but is preferably hydrocarbon solvents such as hexane, heptane, octane, nonane, decane, benzene, toluene, and xylene.

The washing method is not particularly limited provided that it is a method that enables adhered matters on the base material surface to be removed. Examples of the method include a method in which the base material is immersed in an organic solvent as above; a method in which the base material is allowed to stand either under vacuum or in a normal pressure atmosphere to allow adhered matters on the base material surface to evaporate, and a method in which an inert gas such as dry nitrogen gas is used to blow adhered matters off the base material surface. Alternatively, a more preferable method includes ultrasonication of the base material immersed in the aforementioned organic solvent because a better washing effect can be achieved.

Following the step of washing with the organic solvent, it is preferred that a step of drying the base material be further included. The drying method is not particularly limited, and examples of the method include cutting the solution on the base material surface with an air knife and the like, natural drying, and blowing warm air. Since application of heat on an organic thin film formed on the base material surface will more stabilize the organic thin film, the method of blowing warm air is preferred.

It should be noted that, in the case where no heat is applied on the base material in drying the base material, the method for producing an organic thin film of the present invention may not further include a step of applying heat on the base material, but the method preferably further includes a step of applying heat on the base material because the organic thin film will be more stabilized.

The step of bringing the organic thin film forming solution into contact with the base material may not be carried out in a space maintained at a humidity of 40% RH or more, but is preferably carried out in a space maintained at a humidity of 40% RH or more, more preferably carried out in a space maintained at a humidity of 60% RH or more. In such a space, the water content of the organic thin film forming solution is maintained more preferably. In such a space, if base materials are continuously brought into contact with the organic thin film forming solution, denser monolayers can be formed with good reproducibility.

The method for producing an organic thin film according to the present invention can be used either for production of a monolayer or for production of a multilayer film having two or more layers, but can be used particularly suitably for production of a monolayer. Furthermore, this method can be used not only as a method for forming an organic thin film on a base material surface by chemical adsorption, but also as a method for forming an organic thin film on a base material surface by physical adsorption.

By using the method for producing an organic thin film of the present invention described above, monolayers, self-assembled films, chemical adsorption films, and organic thin films combining their properties can be obtained.

The monolayers in the present invention may not be chemical adsorption films or self-assembled films, but are preferably chemical adsorption films and/or self-assembled films. In the present invention, a self-assembled film refers to a film that is formed as an ordered structure without external compelling forces. In the case where molecules that form the organic thin film such as organosilicon compounds form an aggregate in the organic thin aforementioned film forming solution, an organic thin film obtained by using the organic thin film forming solution will be a self-assembled film. The molecules of the aforementioned organosilicon compound are not solvated with the solvent in the organic thin film forming solution and exist solely. In contrast, some of the molecules assemble to form an aggregate. The aggregate can be obtained by treating the organosilicon compound with a compound that can interact with the organosilicon compound and water.

Examples of the configuration of the aggregate include a configuration in which the molecules assemble via intermolecular forces, coordination bonding, hydrogen bonding, or the like between hydrophobic portions or between hydrophilic portions; a configuration in which the molecules that form the film are bonded together via covalent bonding; a configuration in which micelles or the like are formed by other medium such as water that acts as a nucleus or a mediate; and a configuration formed by a combination of these.

The shape of the aggregate is not particularly limited, and may be any shape such as spherical, chain-like, or band-like shapes. The average particle size of the aggregate is not particularly limited, but is preferably in the range from 10 to 1000 nm.

A chemical adsorption film of the present invention is a chemical adsorption film formed on a base material, wherein the film has crystallinity whether the base material is crystalline or not. In this case, the crystallinity may be either polycrystalline or monocrystalline.

EXAMPLES

Hereinbelow, the present invention is described in detail employing Examples, but the technical scope of the present invention is not intended to be limited to these illustrations.

1 Production of an Organosilicon Compound

Example 1

Synthesis of MeO-ODS i) Synthesis of 18-methoxy-1-octadecene

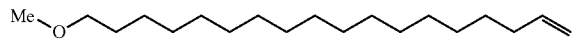 [SMILES: C=CCCCCCCCCCCCCCCCCOC]

To a 200 mL four-necked flask, tetrabutylammonium bromide (TBAB, 0.8 g, 2.48 mmol), methanol (16.9 g, 526 mmol), and sodium hydroxide (4.0 g, 100 mmol) were added, and stirred and dissolved at room temperature. With stirring at room temperature, MIBK (50 mL) and 18-bromo-1-octadecene (16.6 g, 47.0 mmol) were added. After 1 hour of reaction at room temperature, the reactant was further refluxed with heating for 1.5 hours. After the reaction was completed, the reactant was cooled to room temperature, a white precipitate was filtered off, and the reaction liquid was washed with tap water (40 mL) four times. The organic layer was dried over $MgSO_4$. After filtration, the layer was concentrated to dryness to thereby obtain 15.4 g of a crude product.

This was purified with silica gel column chromatography to obtain 11.2 g of 18-methoxy-1-octadecene (39.6 mmol, yield of 84%).

ii) Synthesis of MeO-ODSE

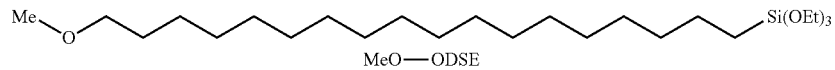

MeO—ODSE

To a 100 mL Schlenk flask under a nitrogen atmosphere, 0.76 g of a 10% Pt/C catalyst (Pt: 0.39 mmol), 18-methoxy-1-octadecene (11.0 g, 39.0 mmol), and triethoxysilane (25.6 g, 156 mmol) were added and stirred at 60° C. for 3 hours.

After the reaction was completed, excess triethoxysilane was removed under reduced pressure. The reactant was diluted with dehydrated toluene (30 mL), and the Pt/C catalyst was removed by filtration to thereby obtain a dark brown solution. To this, 6.2 g of activated carbon (Wako Pure Chemical Industries, Ltd., neutral powder for columns) was added. The solution was allowed to stand at room temperature for 20 minutes, and then, was decolorized by filtration through Celite (No. 545). This filtrate was concentrated under reduced pressure to obtain the desired MeO-ODSE as a light yellow oil (15.21 g, purity by HPLC of 90%).

$^1$H-NMR (CDCl$_3$, 400 MHz) of MeO-ODSE
0.63 (t, 2H), 1.20 (t, 9H), 1.20-1.45 (m, 30H), 1.56 (tt, 2H), 3.33 (s, 3H), 3.36 (t, 2H), 3.83 (q, 6H)

iii) Synthesis of MeO-ODS

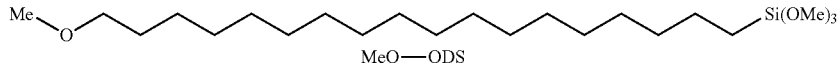

MeO—ODS

To an eggplant flask (200 mL), MeO-ODSE (purity: 90%, 15.21 g) and 10.0 mL of dehydrated toluene were added, and 65 mL of 0.074 mM dry acidic methanol (prepared by adding 0.03 mL of 0.5 M hydrogen chloride methanol solution to 203 mL of dry methanol) was added and stirred at room temperature for 1.5 hours. After concentration with an evaporator under reduced pressure, dry toluene and dry acidic methanol in the same amount as above were added again, and a stirring operation at room temperature for 60 minutes was repeated twice.

After the reaction was completed, concentration under reduced pressure gave MeO-ODS (13.3 g, purity by HPLC: 85%) as a pale yellow oil.

$^1$H-NMR (CDCl$_3$, 400 MHz) of MeO-ODS
0.65 (t, 2H), 1.20-1.45 (m, 30H), 1.56 (tt, 2H), 3.33 (s, 3H), 3.36 (t, 2H), 3.57 (s, 9H)

Example 2

Synthesis of EtO-ODS

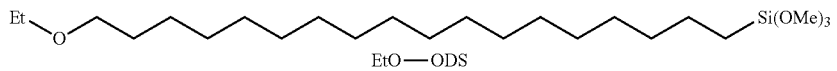

EtO—ODS

EtO-ODS was obtained in the same manner as in Example 1.

$^1$H-NMR (CDCl$_3$, 400 MHz) of EtO-ODS
0.65 (t, 2H), 1.18 (t, 3H), 1.20-1.35 (m, 30H), 1.55 (tt, 2H), 3.39 (t, 2H), 3.45 (q, 2H), 3.55 (s, 9H)

Example 3

Synthesis of Ph-ODS i) Synthesis of 1-phenyl-17-octadecene

To a 200 ml four-necked flask equipped with a thermometer, a condenser, and stirring blades, 20.0 g (60 mmol) of 1-bromo-17-octadecene and 30 ml of dehydrated THF were added, and stirred and dissolved at room temperature.

To this, 61 mg (1.5 mmol) of lithium chloride and 81 mg (0.6 mmol) of copper chloride were added, and stirred and dissolved at room temperature.

To this solution, 71.4 g (112 mmol) of a 2 mol phenyl magnesium bromide solution was added dropwise at 25 to 35° C. to carry out reaction.

After disappearance of 1-bromo-17-octadecene was confirmed with HPLC, 1 g of ethanol was added to decompose unreacted phenyl magnesium bromide, and 50 ml of toluene and 80 ml of 1 N hydrochloric acid were added and stirred.

The mixed liquid was transferred to a separating funnel, and the water layer was separated. After the toluene layer was washed with 50 ml of water twice, toluene was distilled off with an evaporator to obtain 25 g of 1-phenyl-17-octadecene.

ii) Synthesis of 18-phenyl octadecyl trimethoxysilane (Ph-ODS)

To a 50 ml eggplant flask, 5 g (15 mmol) of 1-phenyl-17-octadecene, 7.5 g (46 mmol) of triethoxysilane, and 30 mg of a 10% Pt/C were added and allowed to react at 55 to 65° C. for 4 hours under stirring with a stirrer.

After the reaction was completed, Pt/C was removed by filtration and unreacted triethoxysilane was distilled off under reduced pressure to obtain 8.6 g of 18-phenyl octadecyl triethoxysilane.

The 18-phenyl octadecyl triethoxysilane obtained was subjected to alcohol exchange reaction in methanol having a small quantity of hydrochloric acid dissolved therein to obtain 6.5 g of 18-phenyl octadecyl trimethoxysilane. The purity by HPLC was 89.4%.

$^1$H-NMR (CDCl$_3$, 400 MHz) of Ph-ODS
0.66 (t, 2H), 1.21-1.45 (m, 30H), 1.62 (tt, 2H), 2.62 (t, 2H), 3.62 (s, 9H), 3.86 (t, 2H), 7.15-7.21 (m, 3H), 7.25-7.30 (m, 2H)

2 Formation of an Organic Thin Film 2-1 Preparation of an Organic Thin Film Forming Solution Example 4

Preparation of a MeO-ODS Organic Thin Film Forming Solution

To a 200 ml four-necked flask, 16.1 g (43.0 mmol) of octadecyl trimethoxysilane (manufactured by Gelest, Inc.: purity of 95%) was added at room temperature, and 4.6 g (16.4 mmol) of tetraisopropoxytitanium (manufactured by Nippon Soda Co., Ltd.) was added. The mixture was diluted by adding 77.6 g of toluene. To this solution, 1.7 g of distilled water was added and allowed to react at room temperature for 24 hours to obtain a solution A.

Subsequently, to a 30 ml glass vessel having a lid, the MeO-ODS (3.2 g, purity of 85%, 6.7 mmol) synthesized was added, and 0.12 g (6.7 mmol) of ion exchange water and 0.014 g of the solution A were added, and diluted by adding toluene to provide 15 g of a solution, which was allowed to react at room temperature for 9 days to obtain a hydrolysis product solution.

Then, to a 100 mL four-necked flask, 5 g of the hydrolysis product solution was added at room temperature, and diluted with addition of 145 g of toluene to obtain a chemical adsorption film forming solution B-1.

Example 5

Preparation of an EtO-ODS Organic Thin Film Forming Solution

A chemical adsorption film forming solution B-2 made from EtO-ODS was given in the same manner as in Example 4.

Example 6

Preparation of a Ph-ODS Organic Thin Film Forming Solution

To a 20 ml glass vessel having a lid, 0.98 g (2 mmol) of Ph-ODS, 5.0 g of toluene, 0.04 g (2 mmol) of pure water, and 0.004 g of the solution A were added, and allowed to react at 30° C. for 14 days under stirring with a stirrer to obtain a hydrolysis product solution.

The hydrolysis product solution (1.0 g) was dissolved in toluene (49.0 g) to obtain an organic thin film forming solution B-53.

Comparative Example 1

Preparation of an Octadecyl Trimethoxysilane (ODS) Organic Thin Film Forming Solution To a 1000 ml four-necked flask, 78.9 g (200 mmol) of octadecyl trimethoxysilane (manufactured by Gelest, Inc.: purity of 95%) was added at room temperature, and 0.16 g of the solution A was added. The mixture was diluted by adding 419 g of toluene. To this solution, 3.7 g of distilled water was added and allowed to react at room temperature for 10 days to obtain a hydrolysis product solution.

To a 1000 ml four-necked flask, 20 g of the hydrolysis solution was added at room temperature, and diluted by adding 480 g of toluene to obtain an organic thin film forming solution C-1.

2-2 Formation of an Organic Thin Film

Example 7

A silicon wafer substrate, after ultrasonically washed with pure water and alcohol for pre-washing and further treated with UV-ozone, was dipped in the organic thin film forming solution for a predetermined time. The substrate was then drawn up, ultrasonically washed with an organic solvent, and dried at 60° C. for 20 minutes to form an organic thin film thereon.

3 Evaluation

1) Static Contact Angle Evaluation (Liquid Repellency)

The contact angle was measured using Drop Master 700 (manufactured by Kyowa Interface Science Co., Ltd.), 60 seconds after 5 μl of water or tetradecane (hereinbelow, abbreviated as "TD") was added dropwise onto the surface of each sample using a microsyringe. It should be noted that the lower the liquid repellency (the smaller the contact angle), the higher the wettability.

TABLE 1

| | (Unit: degrees) | |
|---|---|---|
| | TD | Water |
| MeO—ODS | 7 | 83 |
| EtO—ODS | 30 | 88 |
| Ph—ODS | 7 | 90 |
| ODS | 40 | 110 |

2) Dynamic Contact Angle Evaluation: Extension/Contraction Method (Liquid Slippage)

Evaluation was carried out by measuring dynamic contact angle of thin films with Drop Master 700 (manufactured by Kyowa Interface Science Co., Ltd.) using droplets of butyl carbitol acetate. The dynamic contact angle measurement, which is a method performed based on the difference Δ between the advance angle θa and the retreat angle θr of a droplet, is described in Japanese unexamined Patent Application Publication No. 2007-322181 in detail.

TABLE 2

| | BCA | | | TEG | | | Water | | |
|---|---|---|---|---|---|---|---|---|---|
| | θa | θr | Δ | θa | θr | Δ | θa | θr | Δ |
| MeO-ODS | — | — | — | 59 | 44 | 15 | 86 | 67 | 19 |
| EtO-ODS | 34 | 22 | 12 | 71 | 61 | 10 | | | |
| Ph-ODS | — | — | — | 54 | 53 | 1 | — | — | — |
| ODS | 56 | 52 | 4 | 79 | 75 | 4 | 95 | 93 | 2 |

3) Dynamic Contact Angle Evaluation: Falling Angle Method (Lubricity)

The angle at which a droplet starts to fall was measured at room temperature with changing the slope angle of film-deposited substrates. Water was used as the liquid, and the amounts added were as shown in the following table.

TABLE 3

| | (Unit: degrees) Angle at which the water droplet starts to fall | | |
|---|---|---|---|
| | 10 μL | 20 μL | 30 μL |
| MeO—ODS | 27 | 19 | 10 |
| EtO—ODS | 20 | 12 | 8 |
| Ph—ODS | 13 | 8 | 7 |
| ODS | 8 | 4 | 1 |

4) 180° Peel Test (Peelability)

Measuring equipment: Autograph (Shimadzu Table-top Precision Universal Tester AGS-J)
Tape used: Cellotape (registered trademark) manufactured by Nichiban Co., Ltd. (width of 18 mm)
Tension rate: 50 mm/minute
Number of measurements: The measurements were made three times, and the average was calculated.

TABLE 4

| SAM/Si | Average peel stress (mN/mm) | Stress reduction ratio (compared with No SAM) |
|---|---|---|
| No SAM | 299 | 0% |
| MeO—ODS | 213 | 29% |
| EtO—ODS | 168 | 44% |
| Ph—ODS | 93 | 69% |
| ODS | 92 | 69% |

5) Constant Load Friction Test (Slippage)
Measuring equipment: TRIBOGEAR HHS2000 variable load friction and wear test system (HEIDON)
Moving distance: 15 mm, moving rate: 3.0 mm/second Penetrator: SUS sphere (5 mm p), vertical load: 50 g
Number of measurements: five times per substrate
Maximum static friction force ($F_s$): Maximum friction forces at the start of sweep were averaged.
Dynamic friction force ($F_k$): Friction forces after the start of sweep from the point at which the friction force was stabilized to the end of measurement were averaged.
Static friction coefficient ($\mu_s$), dynamic friction coefficient ($\mu_k$): calculated by dividing the friction force by the load

TABLE 5

| SAM/Si | Static friction coefficient | | Dynamic friction coefficient | |
|---|---|---|---|---|
| | $\mu_s$ | Reduction ratio (compared with No SAM) | $\mu_k$ | Reduction ratio (compared with No SAM) |
| No SAM | 1.16 | 0% | 0.48 | 0% |
| MeO—ODS | 0.15 | 87% | 0.09 | 81% |
| Ph—ODS | 0.25 | 78% | 0.12 | 74% |
| ODS | 0.12 | 90% | 0.08 | 83% |

From the results above, the films made from MeO-ODS have a low friction coefficient despite having a high wettability relative to the films made from ODS. The films made from Ph-ODS, in addition to its high wettability, have a high liquid slippage and lubricity as well, and thus are useful for applications requiring wettability.

The invention claimed is:

1. An organic thin film forming solution obtained by mixing
   a) an organosilicon compound represented by formula (I):

$$R-(CH_2)_n-SiX_3 \quad (I)$$

wherein:
   R represents an alkoxy group having 1 to 3 carbon atoms or a phenyl group that optionally has a substituent,
   X represents a hydroxyl group or a hydrolyzable group, and
   n represents any integer from 17 to 24;
   b) a compound that can interact with the organosilicon compound, which is at least one compound selected from the group consisting of:
   metal oxides,
   metal hydroxides,
   partial hydrolysis products of metal alkoxides,
   hydrolysis products obtained by treating metal alkoxides with a two-fold or more equivalent of water,
   chelated or coordinated metal compounds, and
   silanol condensation catalysts, and
   c) water in an organic solvent.

2. A method for forming an organic thin film, comprising the steps of:
   (A) mixing
      a) an organosilicon compound represented by formula (I):

$$R-(CH_2)_n-SiX_3 \quad (I)$$

wherein:
      R represents an alkoxy group having 1 to 3 carbon atoms or a phenyl group that optionally has a substituent,
      X represents a hydroxyl group or a hydrolyzable group, and
      n represents any integer from 17 to 24;
      b) a compound that can interact with the organosilicon compound, which is at least one compound selected from the group consisting of:
      metal oxides,
      metal hydroxides,
      partial hydrolysis products of metal alkoxides,
      hydrolysis products obtained by treating metal alkoxides with a two-fold or more equivalent of water,
      chelated or coordinated metal compounds, and
      silanol condensation catalysts, and
      c) water in an organic solvent to prepare an organic thin film forming solution; and
   (B) bringing the obtained organic thin film forming solution into contact with a substrate.

3. An organic thin film obtained by the method according to claim 2.

4. The organic thin film according to claim 3, wherein the organic thin film is a crystalline monolayer.

* * * * *